US012667692B2

(12) United States Patent     (10) Patent No.:   US 12,667,692 B2

Haldis et al.     (45) Date of Patent:    Jun. 30, 2026

(54) INTERMEDIATE SUCTION CATHETER

(71) Applicant: Sanford Health, Sioux Falls, SD (US)

(72) Inventors: Thomas Haldis, Sioux Falls, SD (US);
Alexander Drofa, Sioux Falls, SD (US)

(73) Assignee: Sanford Health, Sioux Falls, SD (US)

( * ) Notice: Subject to any disclaimer, the term of this
patent is extended or adjusted under 35
U.S.C. 154(b) by 981 days.

(21) Appl. No.: 17/756,944

(22) PCT Filed: Dec. 11, 2020

(86) PCT No.: PCT/US2020/064430
§ 371 (c)(1),
(2) Date: Jun. 6, 2022

(87) PCT Pub. No.: WO2021/119386
PCT Pub. Date: Jun. 17, 2021

(65) Prior Publication Data
US 2023/0001140 A1     Jan. 5, 2023

Related U.S. Application Data

(60) Provisional application No. 62/946,940, filed on Dec.
11, 2019.

(51) Int. Cl.
*A61M 25/00*     (2006.01)

(52) U.S. Cl.
CPC . *A61M 25/0054* (2013.01); *A61M 2025/0004*
(2013.01)

(58) Field of Classification Search
CPC .......... A61M 25/0013; A61M 25/0051; A61M
25/0053; A61M 25/0054; A61M 25/0138;
A61M 2025/0046; A61M 25/0905
See application file for complete search history.

(56) References Cited

U.S. PATENT DOCUMENTS

2006/0121218 A1*   6/2006   Obara ............... A61M 25/0052
    428/34.7
2009/0118704 A1*   5/2009   Sharrow ................. A61L 29/02
    29/605
2010/0331776 A1*   12/2010   Salahieh ........... A61M 25/0138
    604/95.04

(Continued)

OTHER PUBLICATIONS

International Search Report and Written Opinion for corresponding
PCT application No. PCT/US2020/064430 dated Mar. 12, 2021.

*Primary Examiner* — Kami A Bosworth

(74) *Attorney, Agent, or Firm* — McDonnell Boehnen
Hulbert & Berghoff LLP

(57) ABSTRACT

The present disclosure provides a catheter (100) including a
first end (102), a second end (104), and a lumen (106)
extending from the first end to the second end. The catheter
has a first portion (108) arranged at the first end, a second
portion (110) arranged adjacent to the first portion, and a
third portion (112) arranged adjacent to the second portion.
The first portion of the catheter has a first cut pattern in an
exterior surface of the catheter, and the second portion of the
catheter has a second cut pattern in the exterior surface of the
catheter that is different from the first cut pattern. The third
portion of the catheter has a third cut pattern in the exterior
surface of the catheter that is different from the first cut
pattern and the second cut pattern.

27 Claims, 6 Drawing Sheets

(56) References Cited

U.S. PATENT DOCUMENTS

| | | | |
|---|---|---|---|
| 2011/0077620 A1* | 3/2011 | deBeer | A61M 25/0051 |
| | | | 604/524 |
| 2012/0310085 A1* | 12/2012 | Herweck | A61B 8/0841 |
| | | | 604/529 |
| 2015/0119862 A1 | 4/2015 | Cajamarca | |
| 2016/0074627 A1* | 3/2016 | Cottone | A61M 25/0068 |
| | | | 604/510 |
| 2016/0121080 A1 | 5/2016 | Cottone | |
| 2018/0093070 A1* | 4/2018 | Cottone | A61M 25/0021 |
| 2019/0060612 A1 | 2/2019 | Besselink | |
| 2019/0160259 A1 | 5/2019 | Cottone | |
| 2020/0230359 A1* | 7/2020 | Fojtik | A61M 25/0013 |

* cited by examiner

Figure 8:
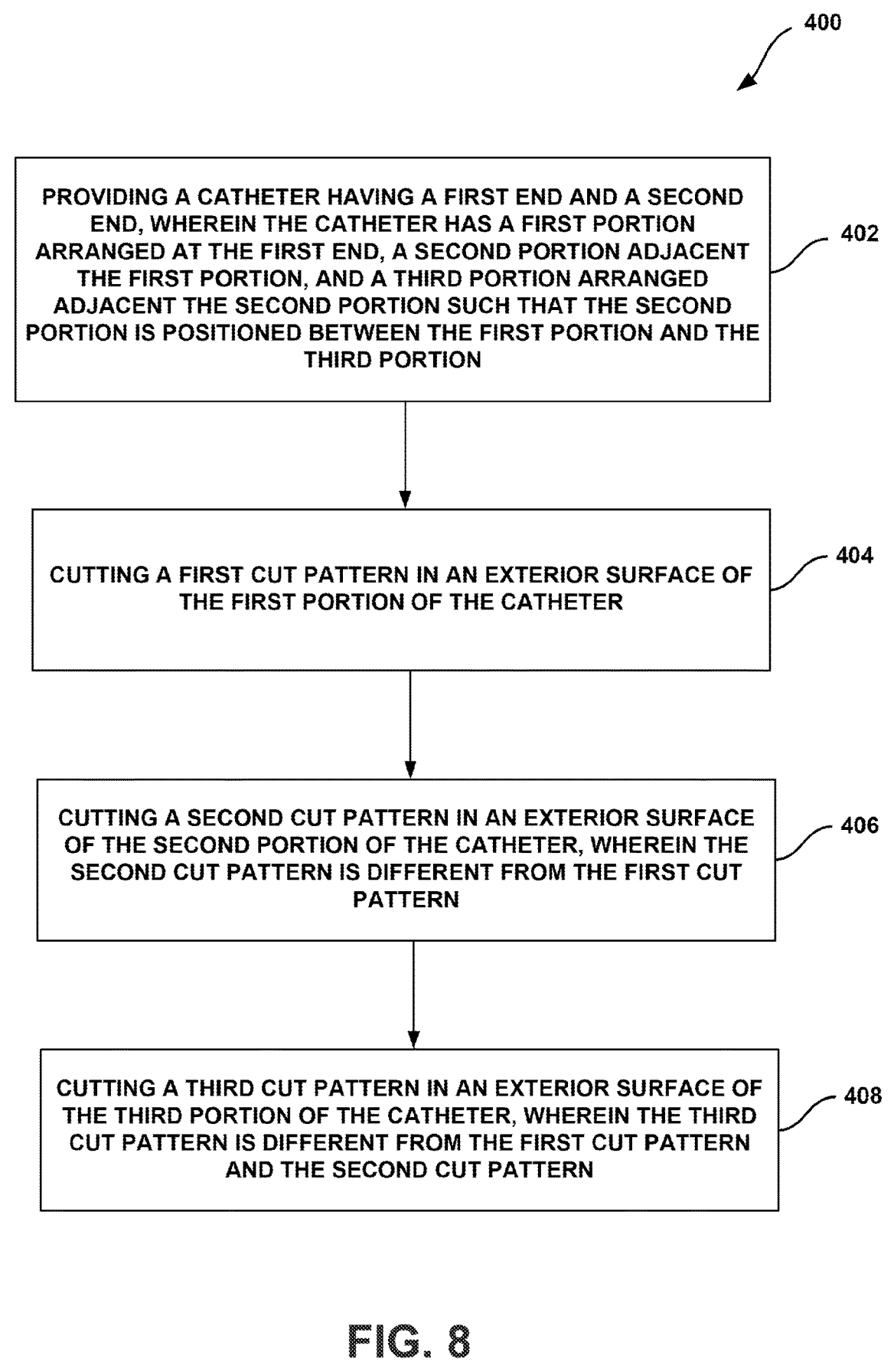

400

PROVIDING A CATHETER HAVING A FIRST END AND A SECOND END, WHEREIN THE CATHETER HAS A FIRST PORTION ARRANGED AT THE FIRST END, A SECOND PORTION ADJACENT THE FIRST PORTION, AND A THIRD PORTION ARRANGED ADJACENT THE SECOND PORTION SUCH THAT THE SECOND PORTION IS POSITIONED BETWEEN THE FIRST PORTION AND THE THIRD PORTION

402

CUTTING A FIRST CUT PATTERN IN AN EXTERIOR SURFACE OF THE FIRST PORTION OF THE CATHETER

404

CUTTING A SECOND CUT PATTERN IN AN EXTERIOR SURFACE OF THE SECOND PORTION OF THE CATHETER, WHEREIN THE SECOND CUT PATTERN IS DIFFERENT FROM THE FIRST CUT PATTERN

406

CUTTING A THIRD CUT PATTERN IN AN EXTERIOR SURFACE OF THE THIRD PORTION OF THE CATHETER, WHEREIN THE THIRD CUT PATTERN IS DIFFERENT FROM THE FIRST CUT PATTERN AND THE SECOND CUT PATTERN

Figure 9:
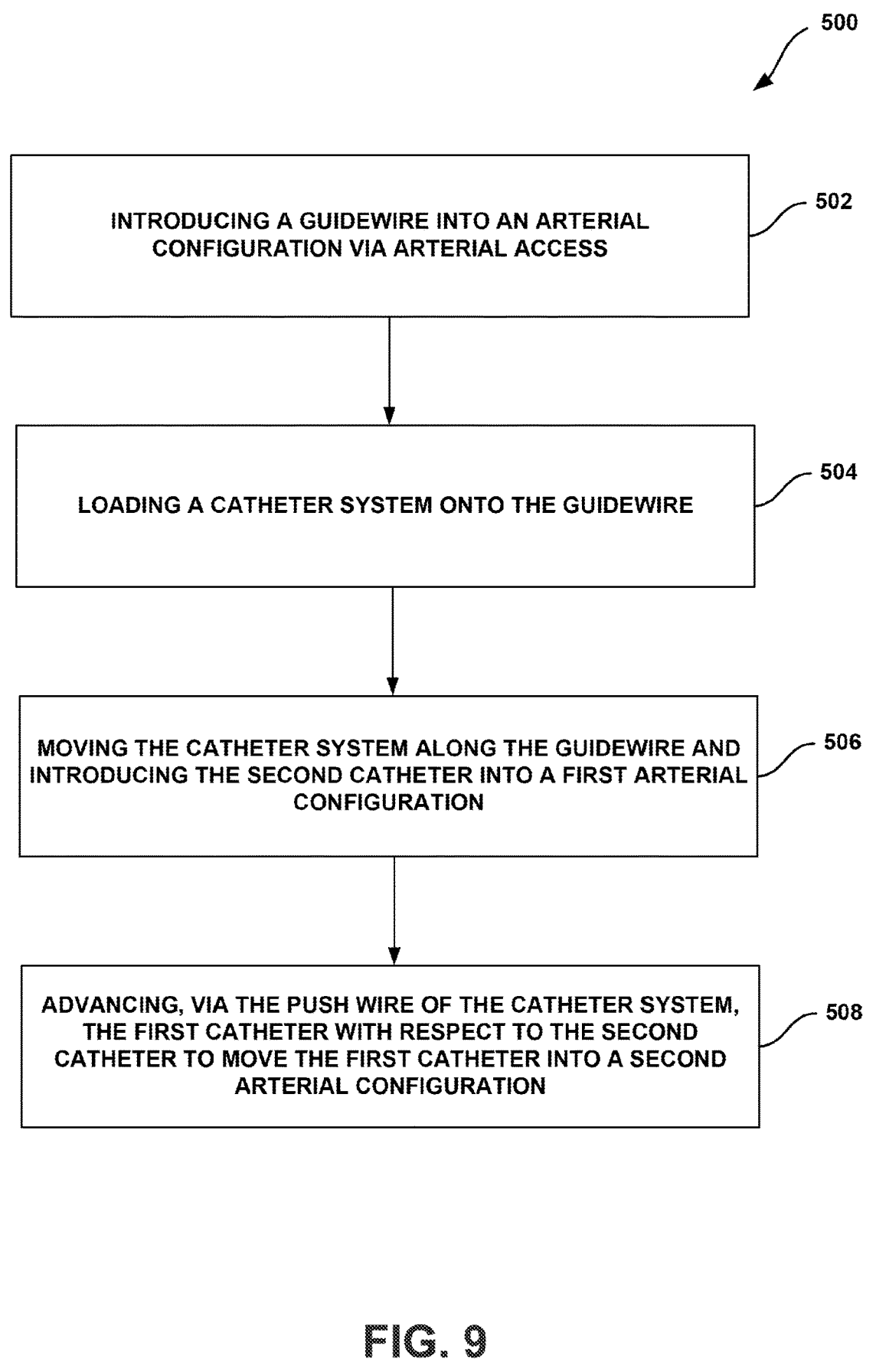

INTRODUCING A GUIDEWIRE INTO AN ARTERIAL
CONFIGURATION VIA ARTERIAL ACCESS

502

LOADING A CATHETER SYSTEM ONTO THE GUIDEWIRE

504

MOVING THE CATHETER SYSTEM ALONG THE GUIDEWIRE AND
INTRODUCING THE SECOND CATHETER INTO A FIRST ARTERIAL
CONFIGURATION

506

ADVANCING, VIA THE PUSH WIRE OF THE CATHETER SYSTEM,
THE FIRST CATHETER WITH RESPECT TO THE SECOND
CATHETER TO MOVE THE FIRST CATHETER INTO A SECOND
ARTERIAL CONFIGURATION

INTERMEDIATE SUCTION CATHETER

CROSS REFERENCE TO RELATED APPLICATION

This application is a U.S. National Phase application of, and claims the benefit of, International (PCT) Application No. PCT/US2020/064430, filed Dec. 11, 2020, which claims priority to U.S. Provisional Application No. 62/946,940 entitled "Intermediate Suction Catheter" filed on Dec. 11, 2019, the contents of each of which are hereby incorporated by reference in their entirety.

BACKGROUND

Cerebral blood flow is critical in human anatomy. If blood flow is blocked to the brain, the tissue that does not receive blood flow will become ischemic and begin to die. The result is either a deficit in cognition, function, or even death. The results are also irreversible if such an ischemia lasts too long. The period of time can vary from patient to patient, but typically if blood flow to the brain is not restored after approximately 4.5 hours, an ischemic stroke may occur. These ischemic strokes can happen in any of the cerebral arteries, but are most common in the middle cerebral artery. Traditionally, such middle cerebral artery acute ischemic strokes have been fatal.

Around 1995, the use of tissue plasminogen activator (tPA), a lytic agent, was introduced as the first treatment for ischemic stroke. The tPA brakes down unorganized acute clot. This procedure reduced mortality from near 100% to 80% and has been the main stay in acute ischemic stroke treatment until just recently. In 2015, a new approach was approved in the United States known as mechanical thrombectomy. In this approach, a stent retriever is deployed within a lesion, the stent struts spread into the clot, then the clot is drawn back into the catheter under suction and removed from the body. This mechanical thrombectomy approach has reduced the mortality rate to around 20% for patients who are treated within the critical time window.

While outcomes are significantly improved, the mechanical thrombectomy procedure is still labor intensive. The mechanical thrombectomy device is either introduced through a femoral or carotid access. If the device is introduced from a femoral access, the operator needs to navigate the aortic anatomy with a special focus on the aortic arch. Aortic arches can be difficult to navigate, especially with type three aortic arches. Once the lesion is reached and crossed, the lesion can be treated. However, reaching the lesion can be challenging due to the tortuous nature of various arteries, such as the cerebral and coronary arteries as examples. The guide catheter which is used to select the target artery is often too stiff and has too large of a diameter to pass the bends in the middle cerebral artery and/or coronary arteries, pulmonary arteries and venous system.

SUMMARY

The present disclosure provides an intermediate catheter portion of a slide guide acute ischemic stroke thrombectomy catheter. The design of the provided intermediate catheter is unique in the neurovascular intervention space in a couple of ways. First, in conjunction with a guide catheter, the intermediate catheter acts as a clot aspiration catheter or a channel for thrombectomy devices. Second, the intermediate catheter is specifically tuned for varying flexibility down length of catheter. Third, the intermediate catheter has an atraumatic tip so as not to damage vasculature. As such, the proposed catheter design is an intermediate catheter uniquely designed to quickly navigate narrow vasculature of the brain and quickly address strokes.

Thus, in a first aspect, the present disclosure provides a catheter including a first end, a second end, and a lumen extending from the first end to the second end. The catheter has a first portion arranged at the first end, a second portion arranged adjacent to the first portion, and a third portion arranged adjacent to the second portion. The first portion of the catheter has a first cut pattern in an exterior surface of the catheter, and the second portion of the catheter has a second cut pattern in the exterior surface of the catheter that is different from the first cut pattern. The third portion of the catheter has a third cut pattern in the exterior surface of the catheter that is different from the first cut pattern and the second cut pattern.

In a second aspect, the present invention provides a device that includes (a) the catheter of the first aspect, and (b) a push wire coupled to the second end of the catheter.

In a third aspect, the present disclosure provides a method that includes (a) providing a catheter having a first end and a second end, wherein the catheter has a first portion arranged at the first end, a second portion arranged at the second end, and a third portion arranged between the first portion and the second portion, (b) cutting a first cut pattern in an exterior surface of the first portion of the catheter, (c) cutting a second cut pattern in an exterior surface of the second portion of the catheter, wherein the second cut pattern is different from the first cut pattern, and (d) cutting a third cut pattern in an exterior surface of the third portion of the catheter, wherein the third cut pattern is different from the first cut pattern and the second cut pattern.

In a fourth aspect, the present disclosure provides a catheter system including (a) a first catheter according to the first aspect, wherein the first catheter has a first diameter, (b) a second catheter having a first end and a second end, wherein the second catheter has a second diameter that is greater than the first diameter of the first catheter, and wherein the first catheter is positioned at least partially within a lumen of the second catheter and is moveable relative to the second catheter, and (c) a push wire having a first end and a second end, wherein the first end of the push wire is coupled to the second end of the first catheter.

In a fifth aspect, the present disclosure provides a method comprising (a) introducing a guidewire into an arterial configuration via arterial access, (b) loading the catheter system of the fourth aspect onto the guidewire, (c) moving the catheter system along the guidewire and introducing the second catheter into a first arterial configuration, and (d) advancing, via the push wire of the catheter system, the first catheter with respect to the second catheter to move the first catheter into a second arterial configuration.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1 illustrates a side view of a catheter system, according to an example embodiment.

FIG. 8 is a flow chart depicting functions that can be carried out in accordance with example embodiments of the disclosed methods.

FIG. 9 is another flow chart depicting functions that can be carried out in accordance with example embodiments of the disclosed methods.

DETAILED DESCRIPTION OF THE INVENTION

Figures 1, 2:
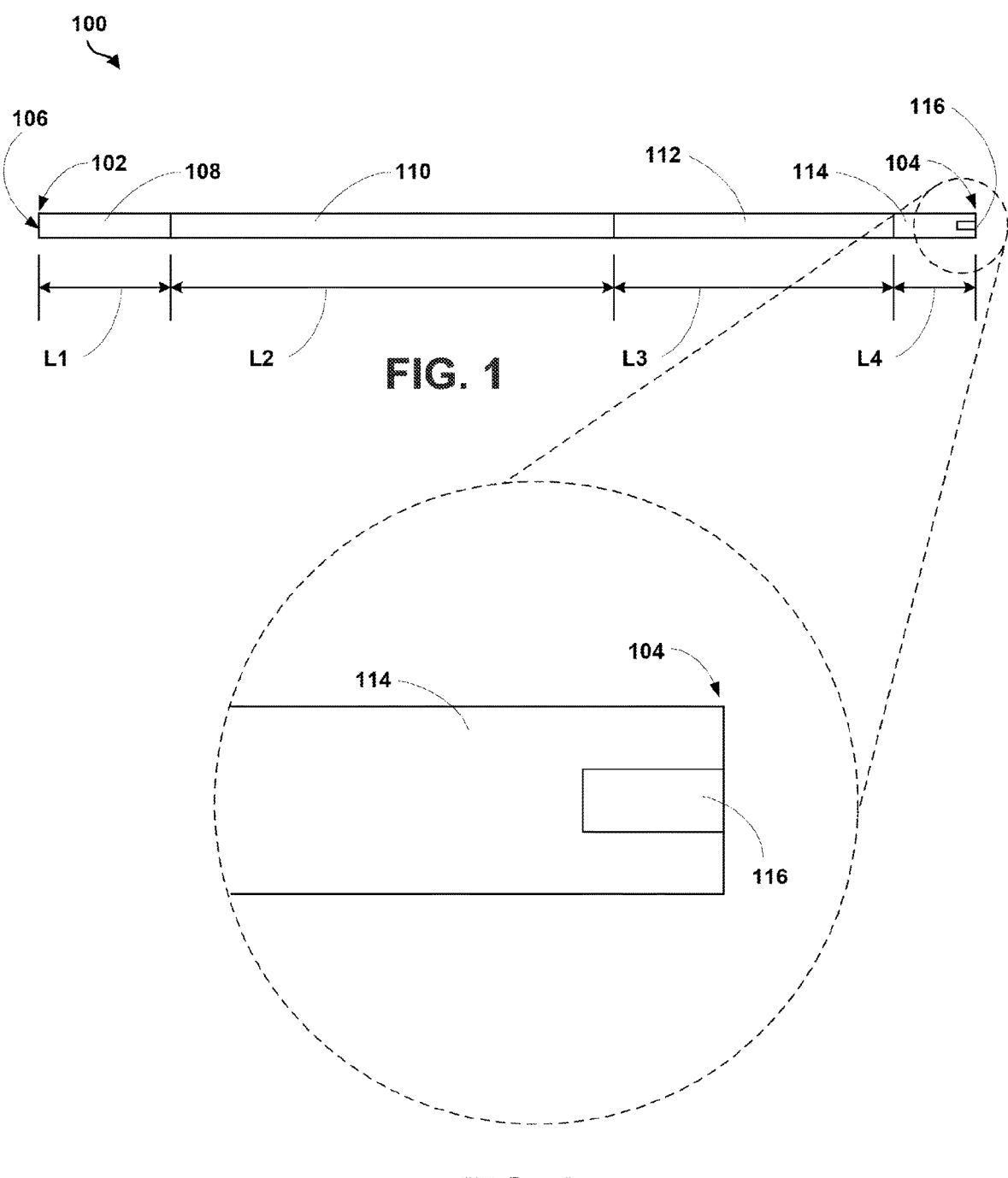
FIG. 1 illustrates a side view of a catheter, according to an example embodiment.
FIG. 2 illustrates a zoomed in view of the second end of the catheter of FIG. 1, according to an example embodiment.

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. One of ordinary skill in the art will readily understand that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, a "catheter" is an apparatus that is connected to a deployment mechanism and houses a medical device that can be delivered over a guidewire. The catheter may include a guidewire lumen for over-the-wire guidance and may be used for delivering a device to a target lumen. A catheter can have braided metal strands within the catheter wall for increased structural integrity. The structural elements of the catheter tip can be bonded or laser welded to the braided strands of the catheter to improve the performance characteristics of the catheter tip.

As used herein, a "guidewire" is an elongated cable comprised of one or more biocompatible materials including metals and polymers. Guidewires may be used for selecting target lumens and guiding catheters to target deployment locations. Guidewires are typically defined as wires used independently of other devices that do not come as part of an assembly.

As used herein, a "stent retriever" is a device, like a stent, that is advanced through emboli and allowed to expand and embed in the emboli that may then be retracted to restore blood flow and aid thrombectomy in acute embolic stroke.

As used herein, "lumen" refers to a passage within an arterial structure, such as the pulmonary arteries or a passage within the tubular housings or catheters through which the guidewire may be disposed.

As used herein, "deployment" refers to when a catheter has been positioned in the target lumen and is actively being used.

As used herein, with respect to measurements, "about" means +/−5%.

As used herein, "coupled" means associated directly as well as indirectly. For example, a member A may be directly associated with a member B, or may be indirectly associated therewith, e.g., via another member C. It will be understood that not all relationships among the various disclosed elements are necessarily represented.

Unless otherwise indicated, the twits "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, device, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, device, structure, article, element, component, or hardware which enable the system, apparatus, device, structure, article, element, component, or hardware to perform the specified function without further modification. For purposes of this disclosure, a system, apparatus, device, structure, article, element, component, or hardware described as being "configured to" perform a particular function may additionally or alternatively be described as being "adapted to" and/or as being "operative to" perform that function.

With reference to the Figures, FIG. 1 illustrates a catheter 100, according to an example embodiment. As shown in FIG. 1, the catheter 100 includes a first end 102 and a second end 104. The catheter also includes a lumen 106 extending from the first end 102 to the second end 104. The catheter 100 has a first portion 108 arranged at the first end 102, a second portion 110 arranged adjacent to the first portion 108, and a third portion 112 arranged adjacent to the second portion 110. As shown in FIG. 1, the second portion 110 is positioned between the first portion 108 and the third portion 112. The catheter further includes a fourth portion 114 arranged at the second end 104 and adjacent to the third portion 112. As shown in FIG. 1, the third portion 112 is positioned between the second portion 110 and the fourth portion 114. FIG. 2 illustrates a zoomed in view of the second end 1043 of the catheter 100. As shown in FIG. 2, the second end 104 of the catheter 100 may include a slot 116. In one example, the slot 116 is about 0.018 inches long in a direction from the second end 104 towards the first end 102 and about 0.008 inches wide.

In use, the slot 116 may be used to couple the catheter 100 to a push wire 202, as discussed in additional detail below. In one particular example, the push wire 202 is welded to the catheter 100 in the slot 116. The slot 116 provides a removal of material at the second end 104 of the catheter 100 such that when the catheter 100 is coupled to the push wire 202 the inner diameter and the maximum outer diameter of the catheter 100 remains uniform along the length of the catheter 100 from the first end 102 to the second end. As such, when the catheter 100 is coupled to the push wire 202 in the slot 116, there is not too much material on the inner diameter or the outer diameter of the catheter 100 which would interfere with the required space for a clot retriever or for the catheter 100 to fit inside a guide catheter, respectively. The catheter 100 may be configured to be housed inside of such a guide catheter, and the catheter 100 may be actuated in and out of the guide catheter via the push wire 202 coupled on to the second end 104 of the catheter 100.

The catheter 100 illustrated in FIG. 1 may comprise a stainless steel material, such as 304 stainless steel as a non-limiting example. Further, the catheter 100 may be cut with a specific pattern to achieve varying flexibility down the length of the catheter 100. In particular, the first portion 108 of the catheter 100 has a first cut pattern in an exterior surface of the catheter 100, the second portion 110 of the catheter 100 has a second cut pattern in the exterior surface of the catheter 100 that is different from the first cut pattern, and the third portion 112 of the catheter 100 has a third cut pattern in the exterior surface of the catheter 100 that is different from the first cut pattern and the second cut pattern. In one example, the fourth portion 114 does not include a cut pattern in the exterior surface of the catheter 100 (other than the slot 116 discussed above). As such, the fourth portion 114 is solid (aside from the slot 116) to provide a gradual transition of flexibility to avoid creating a stress riser that would exist if the push wire 202 were coupled to a more flexible cut pattern.

Figures 3, 4:
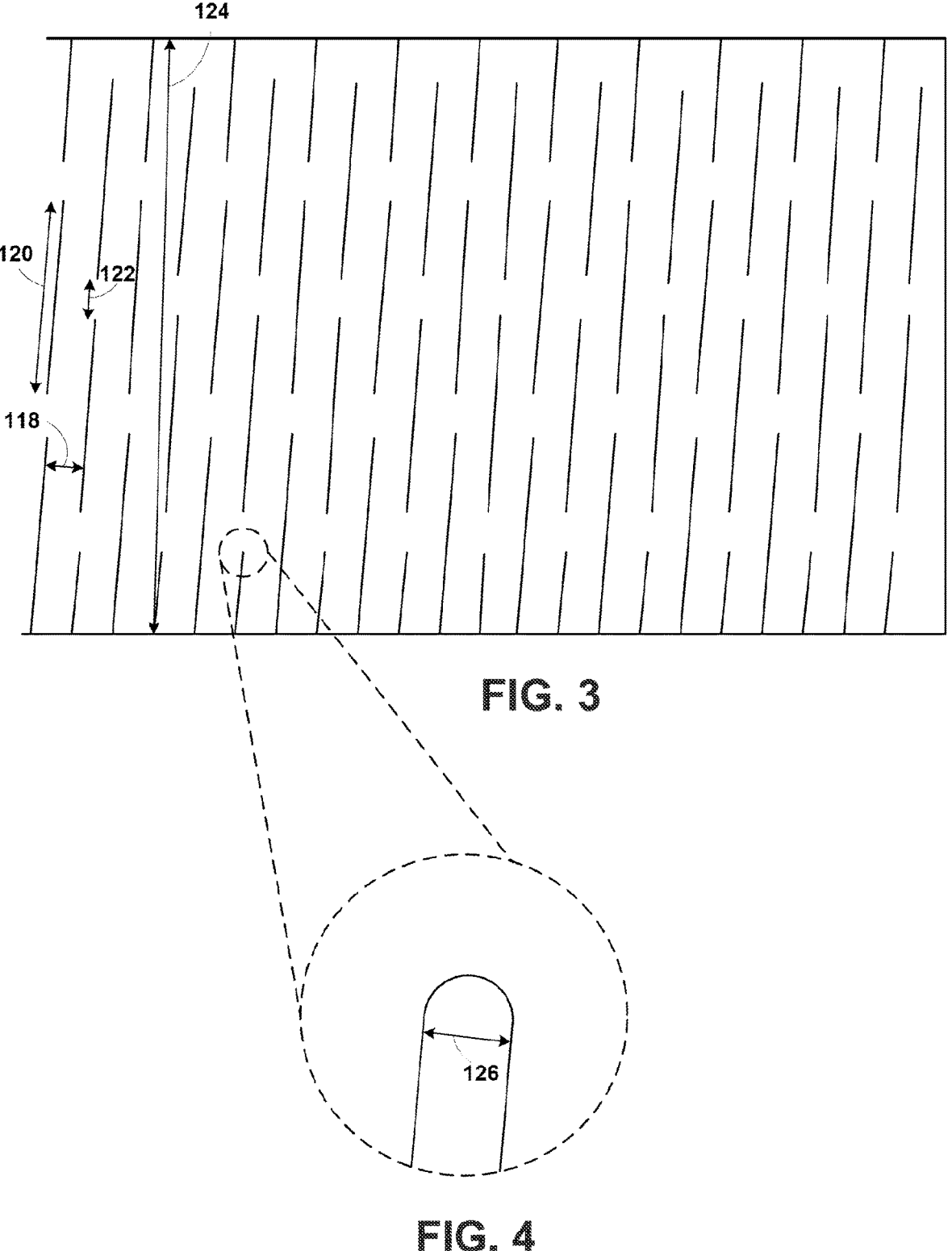
FIG. 3 illustrates a cut pattern, according to an example embodiment.
FIG. 4 illustrates a zoomed in view of the cut pattern of FIG. 3, according to an example embodiment.

As used herein, a "cut pattern" refers to a pattern in which material is removed from the exterior surface of the catheter 100 to thereby change the flexibility of the catheter 100. FIG. 3 illustrates various parameters that make up a given cut pattern. As shown in FIG. 3, the cut pattern may include a pitch 118, degrees cut 120, degrees uncut 122, a circumference 124, and a cut width 126 (a zoomed in view of which can be seen in FIG. 4). Another parameter that may be used to define a given cut pattern is cuts per rotation (CPR), which is calculated using the simple formula of CPR=360/(degrees cut+degrees uncut).

In one example, a pitch 118 of the first cut pattern is constant (e.g., the pitch 118 of material removed from the exterior surface of the first portion 108 of the catheter 100 is constant), a pitch 118 of the second cut pattern transitions along a length of the second portion 110 (e.g., the pitch 118 of material is removed from the exterior surface of the second portion 110 varies), and a pitch 118 of the third cut pattern transitions along a length of the third portion 112 (e.g., the pitch 118 of material is removed from the exterior surface of the third portion 112 varies). In one particular example, the pitch 118 of the first cut pattern is about 0.004 inches along a length of the first portion 108, the pitch 118 of the second cut pattern transitions from about 0.004 inches to about 0.010 inches in a direction from the first end 102 to the second end 104 (e.g., the pitch 118 of the second cut pattern is 0.004 inches where the first portion 108 and second portion 110 meet and the pitch 118 of the second cut pattern is 0.010 inches where the second portion 110 and third portion 112 meet), and the pitch 118 of the third portion 112 transitions from about 0.010 inches to about 0.016 inches in a direction from the first end 102 to the second end 104 (e.g., the pitch 118 of the third cut pattern is 0.010 inches where the second portion 110 and third portion 112 meet and the pitch 118 of the third cut pattern is 0.016 inches where the third portion 112 and fourth portion 114 meet). In general, all other factors remaining the same, as the pitch

118 of the cut pattern increases, the flexibility of the catheter 100 also increases as more material is removed when the pitch 118 increases.

In one example, the pitch 118 of the second cut pattern transitions linearly from about 0.004 inches to about 0.010 inches in a direction from the first end 102 to the second end 104. In another example, the pitch 118 of the second cut pattern transitions non-linearly from about 0.004 inches to about 0.010 inches in a direction from the first end 102 to the second end 104. In one example, the pitch 118 of the third portion 112 transitions linearly from about 0.010 inches to about 0.016 inches in a direction from the first end 102 to the second end 104. In another example, the pitch 118 of the third portion 112 transitions non-linearly from about 0.010 inches to about 0.016 inches in a direction from the first end 102 to the second end 104.

In one example, a CPR of the first cut pattern is different than a CPR of the second cut pattern and a CPR of the third cut pattern. In one particular example, the CPR of the first cut pattern is about 1.5, and the CPR of the second cut pattern and the CPR of the third cut pattern is about 2.5. In general, all other factors remaining the same, as the CPR of the cut pattern decreases, the flexibility of the catheter 100 increases as more material is removed when the CPR is less. Thus, when the CPR of the first cut pattern is about 1.5, and the CPR of the second cut pattern and the CPR of the third cut pattern is about 2.5, more material is removed from the first end 102 of the catheter 100, therefore increasing flexibility. Increased flexibility of the first end 102 (distal end) of the catheter 100 may be beneficial to provide an atraumatic tip when in use.

In one example, a length L1 of the first portion 108 of the catheter 100 ranges from about 1 cm to about 5 cm, and is preferably about 3 cm, a length L2 of the second portion 110 of the catheter 100 ranges from about 10 cm to about 15 cm, and is preferably about 13.5 cm, a length L3 of the third portion 112 of the catheter 100 ranges from about 7.5 cm to about 12.5 cm, and is preferably about 8.373 cm, and a length L4 of the fourth portion 114 of the catheter 100 ranges from about 0.01 cm to about 2 cm, and is preferably about 0.127 cm.

As shown in FIG. 4, the catheter 100 has an inner diameter 128 and an outer diameter 130. The inner diameter 128 of the catheter 100 is constant from the first end 102 to the second end 104. The inner diameter 128 may range from about 0.05 to about 0.1 inches, and preferably is about 0.072 inches. The outer diameter 130 may include a plurality of cuts along the length of the catheter 100 which comprise the cut patterns discussed above. As such, the outer diameter 130 may vary along the length of the catheter 100. In the regions in which there no cuts made, the outer diameter 130 of the catheter may range from about 0.05 to about 0.1 inches, and preferably is about 0.083 inches.

In one example, the catheter 100 includes a polymer membrane surrounding at least a portion of the exterior surface of the catheter 100. The polymer membrane may be about 0.00015 inches thick. In one specific example, the polymer membrane comprises expanded polytetrafluoroethylene (ePTFE). In one example, the polymer membrane is wrapped around the catheter 100. Such a wrapping process may be repeated twice, wrapped once in each direction (distal to proximal and proximal to distal), prior to sintering the covered catheter 100. Further, the catheter 100 may include a lubricious coating on at least a portion of the exterior surface of the catheter 100. In one specific example, the lubricious coating comprises a fluorinated ethylene propylene (FEP) spray coating.

Figure 5:
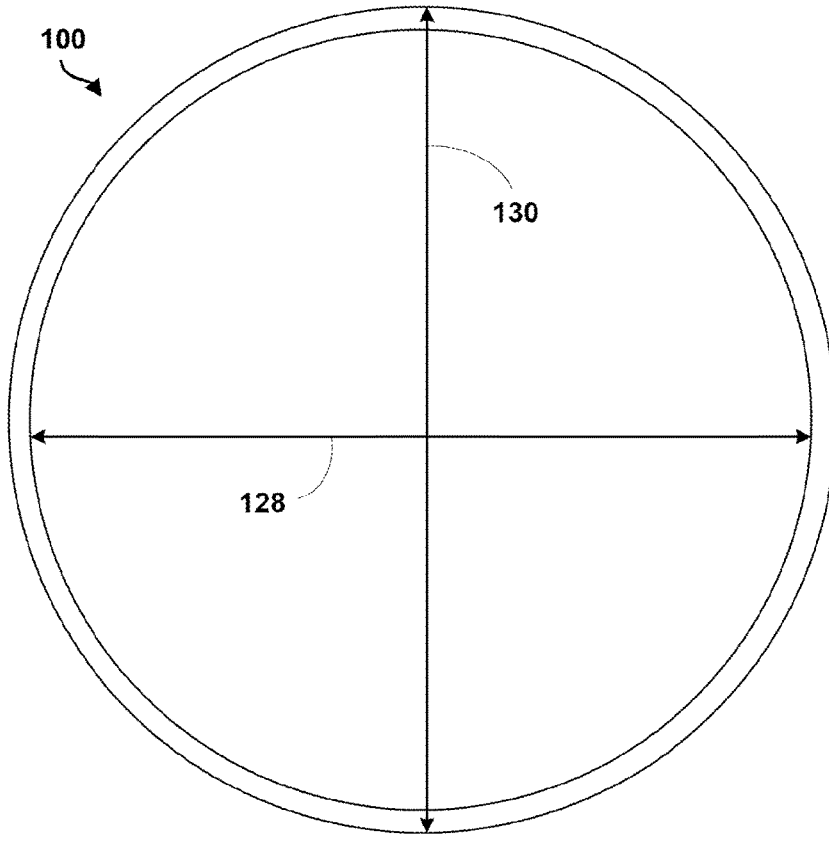
FIG. 5 illustrates a cross-sectional view of the catheter of FIG. 1, according to an example embodiment.

FIG. 5 illustrates a device 200, according to an example embodiment. As shown in FIG. 5, the device 200 includes the catheter 100 according to any of the embodiment discussed above in relation to FIGS. 1-4, and a push wire 202 coupled to the second end 104 of the catheter 100. As discussed above, the second end 104 of the catheter 100 may include a slot 116 cut therein that may be used to couple the catheter 100 to a push wire 202. In one particular example, the push wire 202 is welded to the catheter 100 in the slot 116. The catheter 100 may be configured to be housed inside of a guide catheter, and the catheter 100 may be actuated in and out of the guide catheter via the push wire 202 coupled on to the second end 104 of the catheter 100.

Figure 6:
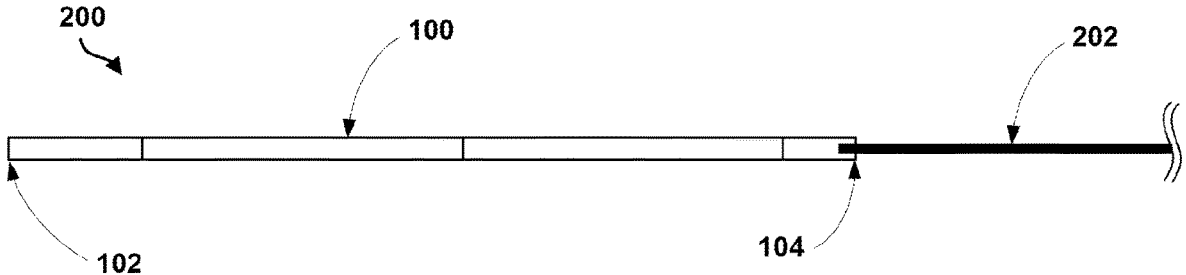
FIG. 6 illustrates a side view of a device, according to an example embodiment.
Figure 7:
Figure 7:
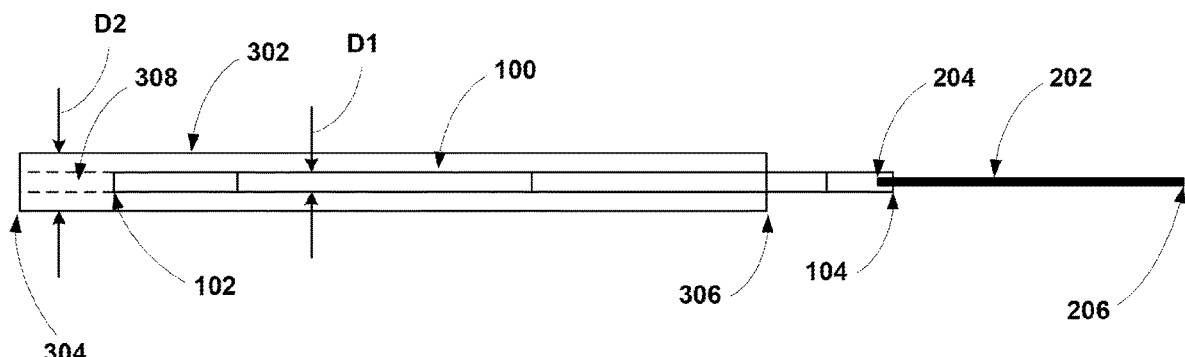

FIG. 6 illustrates a catheter system 300, according to an example embodiment. As shown in FIG. 6, the catheter system 300 includes a first catheter 100 according to any of the embodiment discussed above in relation to FIGS. 1-4. The first catheter 100 has a first diameter D1. The catheter system 300 further includes a second catheter 302 having a first end 304 and a second end 306. In one example, the second catheter 302 may comprise a guide catheter, as discussed above. The second catheter 302 has a second diameter D2 that is greater than the first diameter D1 of the first catheter 100. The first catheter 100 is positioned at least partially within a lumen 308 of the second catheter 302 and is moveable relative to the second catheter 302. The catheter system 300 further includes a push wire 202 having a first end 204 and a second end 206. The first end 204 of the push wire 202 is coupled to the second end 104 of the first catheter 100, as discussed in additional detail above. The first catheter 100 may be actuated in and out of the second catheter 302 via the push wire 202.

FIG. 8 is a block diagram of an example method for manufacturing a catheter. In one example, method 400 shown in FIG. 8 presents an embodiment of a method that could be used to manufacture the catheter 100 of FIGS. 1-7, as described above. Method 400 may include one or more operations, functions, or actions as illustrated by one or more of blocks 402-408. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Initially, at block 402, the method 400 includes providing a catheter 100 having a first end 102 and a second end 104, wherein the catheter 100 has a first portion 108 arranged at the first end 102, a second portion 110 arranged adjacent to the first portion 108, and a third portion 112 arranged adjacent to the second portion 110 such that the second portion 110 is arranged between the first portion 108 and the third portion 112.

At block 404, the method 400 includes cutting a first cut pattern in an exterior surface of the first portion 108 of the catheter 100. At block 406, the method 400 includes cutting a second cut pattern in an exterior surface of the second portion 110 of the catheter 100, where the second cut pattern is different from the first cut pattern. At block 408, the method 400 includes cutting a third cut pattern in an exterior surface of the third portion 112 of the catheter 100, where the third cut pattern is different from the first cut pattern and the second cut pattern.

In one example, a pitch of the first cut pattern is constant, a pitch of the second cut pattern transitions along a length of the second portion 110, and a pitch of the third cut pattern transitions along a length of the third portion 112. In one such example, the pitch of the first cut pattern is about 0.004 inches along a length of the first portion 108, the pitch of the second cut pattern transitions from about 0.004 inches to about 0.010 inches in a direction from the first end 102 to the second end 104, and the pitch of the third cut pattern transitions from about 0.010 inches to about 0.016 inches in a direction from the first end 102 to the second end 104.

In one example, a CPR of the first cut pattern is different than a CPR of the second cut pattern and a CPR of the third cut pattern. In one such example, the CPR of the first cut pattern is about 1.5, and wherein the CPR of the second cut pattern and the CPR of the third cut pattern is about 2.5.

In one example, the method 400 further includes cutting a slot 116 in the second end 104 of the catheter 100.

In one example, the method 400 further includes wrapping a polymer membrane around at least a portion of the exterior surface of the catheter 100. In one such example, wrapping the polymer membrane around at least a portion of the exterior surface of the catheter comprises (i) wrapping the polymer membrane around the exterior surface of the catheter 100 from the first end 102 to the second end 104 to provide a first layer of polymer membrane, and (ii) wrapping the polymer membrane around the exterior surface of the catheter 100 from the second end 104 to the first end 102 to provide a second layer of polymer membrane.

In one example, the method 400 further includes spraying a lubricious coating on at least a portion of the exterior surface of the catheter 100.

FIG. 9 is a block diagram of an example method for using a catheter system. In one example, method 500 shown in FIG. 9 presents an embodiment of a method that could be performed by the catheter system 300 of FIG. 7, as described above. Method 500 may include one or more operations, functions, or actions as illustrated by one or more of blocks 502-508. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Initially, at block 502, the method 500 includes introducing a guidewire into an arterial configuration via arterial access. At block 504, the method 500 includes loading the catheter system 300 onto the guidewire. At block 504, the method 500 includes moving the catheter system 300 along the guidewire and introducing the second catheter 302 into a first arterial configuration. At block 506, the method 500 includes advancing, via the push wire 202 of the catheter system 300, the first catheter 100 with respect to the second catheter 302 to move the first catheter 100 into a second arterial configuration.

In one example, the method 500 further includes inflating a balloon coupled to the first end 304 of the second catheter 302. In another example, the method 500 further includes advancing a treatment solution out of the first catheter 100 and into the second arterial configuration. In another example, the method 500 further includes advancing a stent retriever though a third catheter and into the second arterial configuration or a third arterial configuration. In another example, the method 500 further includes advancing a coronary stent through the first catheter 100 and into the second arterial configuration. In another example, the method 500 further includes advancing a clot retrieval device through the first catheter 100 for pulmonary and venous thrombectomy.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A catheter comprising:
a first end, a second end, and a lumen extending from the first end to the second end, wherein the catheter has a first portion arranged at the first end, a second portion arranged adjacent to the first portion, a third portion arranged adjacent to the second portion, and a fourth portion arranged at the second end and adjacent to the third portion, wherein the first portion of the catheter has a first cut pattern in an exterior surface of the catheter, wherein the second portion of the catheter has a second cut pattern in the exterior surface of the catheter that is different from the first cut pattern, wherein the third portion of the catheter has a third cut pattern in the exterior surface of the catheter that is different from the first cut pattern and the second cut pattern, wherein the fourth portion does not include a cut pattern, wherein the fourth portion includes a slot, and wherein an outer circumference of the fourth portion is uninterrupted but for the slot.

2. The catheter of claim 1, wherein the slot is about 0.018 inches long in a direction from the second end towards the first end and about 0.008 inches wide.

3. The catheter of claim 1, wherein a pitch of the first cut pattern is constant, wherein a pitch of the second cut pattern transitions along a length of the second portion, and wherein a pitch of the third cut pattern transitions along a length of the third portion.

4. The catheter of claim 3, wherein the pitch of the first cut pattern is about 0.004 inches along a length of the first portion, wherein the pitch of the second cut pattern transitions from about 0.004 inches to about 0.010 inches in a direction from the first end to the second end, and wherein the pitch of the third cut pattern transitions from about 0.010 inches to about 0.016 inches in a direction from the first end to the second end.

5. The catheter of claim 1, wherein a cuts per rotation (CPR) of the first cut pattern is different than a CPR of the second cut pattern and a CPR of the third cut pattern.

6. The catheter of claim 5, wherein the CPR of the first cut pattern is about 1.5, and wherein the CPR of the second cut pattern and the CPR of the third cut pattern is about 2.5.

7. The catheter of claim 1, wherein a length of the first portion of the catheter ranges from about 1 cm to about 5 cm, wherein a length of the second portion of the catheter ranges from about 10 cm to about 15 cm, and wherein a length of the third portion of the catheter ranges from about 7.5 cm to about 12.5 cm.

8. The catheter of claim 1, wherein the catheter has an inner diameter that is constant from the first end to the second end.

9. The catheter of claim 8, wherein the inner diameter is about 0.072 inches.

10. The catheter of claim 1, further comprising a polymer membrane surrounding at least a portion of the exterior surface of the catheter.

11. The catheter of claim 10, wherein the polymer membrane is about 0.00015 inches thick.

12. The catheter of claim 1, further comprising a lubricious coating on at least a portion of the exterior surface of the catheter.

13. The catheter of claim 1, wherein the catheter comprises a stainless steel material.

14. The catheter of claim 1, wherein a push wire is coupled to the fourth portion in the slot.

15. The catheter of claim 14, wherein the push wire is welded to the catheter.

16. The catheter of claim 1, wherein a maximum outer diameter of the fourth portion does not exceed a maximum outer diameter of the third portion.

17. The catheter of claim 1, wherein a maximum outer diameter of the catheter remains uniform along a length of the catheter from the first end to the second end.

18. The catheter of claim 1, further comprising a polymer membrane, wherein the polymer membrane is wrapped around at least a portion of the catheter.

19. The catheter of claim 18, wherein the polymer membrane comprises expanded polytetrafluoroethylene.

20. A device comprising:
the catheter of claim 1; and
a push wire coupled to the second end of the catheter.

21. A catheter system comprising:
a catheter according to claim 1, wherein the catheter is a first catheter and the first catheter has a first diameter;
a second catheter having a first end and a second end, wherein the second catheter has a second diameter that is greater than the first diameter of the first catheter, and wherein the first catheter is positioned at least partially within a lumen of the second catheter and is moveable relative to the second catheter; and
a push wire having a first end and a second end, wherein the first end of the push wire is coupled to the second end of the first catheter.

22. A method comprising:
introducing a guidewire into an arterial configuration via arterial access;
loading the catheter system according to claim 21 onto the guidewire;
moving the catheter system along the guidewire and introducing the second catheter into a first arterial configuration; and
advancing, via the push wire of the catheter system, the first catheter with respect to the second catheter to move the first catheter into a second arterial configuration.

23. The method of claim 22, further comprising:
inflating a balloon coupled to the first end of the second catheter.

24. The method of claim 22, further comprising:
advancing a treatment solution out of the first catheter and into the second arterial configuration.

25. The method of claim 22, further comprising:
advancing a stent retriever though a third catheter and into the second arterial configuration or a third arterial configuration.

26. The method of claim 22, further comprising:
advancing a coronary stent through the first catheter and into the second arterial configuration.

27. The method of claim 22, further comprising:
advancing a clot retrieval device through the first catheter for pulmonary and venous thrombectomy.

* * * * *